United States Patent
Riaz

(10) Patent No.: US 8,858,535 B2
(45) Date of Patent: Oct. 14, 2014

(54) CATHETER

(76) Inventor: Ahmad Riaz, Claregalway (IE)

( * ) Notice: Subject to any disclaimer, the term of this patent is extended or adjusted under 35 U.S.C. 154(b) by 143 days.

(21) Appl. No.: 12/997,631

(22) PCT Filed: Jun. 12, 2009

(86) PCT No.: PCT/EP2009/004229
§ 371 (c)(1),
(2), (4) Date: Jan. 25, 2011

(87) PCT Pub. No.: WO2010/142310
PCT Pub. Date: Dec. 16, 2010

(65) Prior Publication Data
US 2011/0118704 A1 May 19, 2011

(30) Foreign Application Priority Data
Jun. 12, 2008 (IE) .................................. S2008/0485

(51) Int. Cl.
*A61M 27/00* (2006.01)
*A61M 25/10* (2013.01)
*A61M 25/04* (2006.01)

(52) U.S. Cl.
CPC ........... *A61M 25/04* (2013.01); *A61M 25/1002* (2013.01); *A61M 27/00* (2013.01); *A61M 2025/1093* (2013.01); *A61M 2025/1065* (2013.01)
USPC ....................................................... 604/544

(58) Field of Classification Search
CPC . A61M 5/1723; A61M 5/172; A61M 5/1002; A61M 25/104; A61M 25/0116; A61M 25/0155; A61M 2025/1052; A61M 25/10; A61M 25/0147; A61M 25/0136; A61M 25/0122; A61M 3/0279
USPC ............. 604/96.01, 95.01, 95.02, 95.03, 509, 604/103.7, 544, 30, 39–43
See application file for complete search history.

(56) References Cited

U.S. PATENT DOCUMENTS

| | | | |
|---|---|---|---|
| 3,253,594 A | 5/1966 | Matthews et al. | |
| 4,243,040 A | 1/1981 | Beecher | |
| 5,308,319 A * | 5/1994 | Ide et al. | 600/18 |
| 6,146,401 A | 11/2000 | Yoon et al. | |
| 6,905,490 B2 * | 6/2005 | Parodi | 604/509 |
| 7,097,039 B2 * | 8/2006 | Muis et al. | 206/564 |
| 2006/0041228 A1 | 2/2006 | Vo et al. | |
| 2008/0097509 A1 * | 4/2008 | Beyar et al. | 606/192 |
| 2011/0125132 A1 * | 5/2011 | Krolik et al. | 604/509 |
| 2011/0190727 A1 * | 8/2011 | Edmunds et al. | 604/509 |

FOREIGN PATENT DOCUMENTS

WO 82/03557 10/1982

OTHER PUBLICATIONS

PCT International Search Report for PCT Application No. PCT/EP2009/004229.

* cited by examiner

*Primary Examiner* — Jackie Tan-Uyen T Ho
*Assistant Examiner* — Mark Wardas
(74) *Attorney, Agent, or Firm* — Gardner, Linn, Burkhart & Flory, LLP

(57) ABSTRACT

The present invention is concerned with a catheter which includes an inflatable balloon operable to retain the catheter in position during use, and which is located and configured to both reduce discomfort during use by preventing contact between the end of the catheter and the urinary tract/bladder wall, and reduce the force required to remove the catheter by reducing cuffing of the collapsed balloon.

14 Claims, 8 Drawing Sheets

CATHETER

FIELD OF THE INVENTION

This invention relates to a catheter, in particular, an indwelling catheter, which finds utility in a number of catheterisation practices, including urinary catheterisation.

BACKGROUND OF THE INVENTION

Catheters find particular utility in the medical field where they are used as an instrument for accessing a body cavity, duct, or vessel, to allow drainage or injection of fluids, or access by surgical instruments.

In urinary catheterisation, for example, the distal tip of the catheter is inserted into the urethra of a patient and a balloon is inflated to retain the catheter. Once inserted, the distal tip of the catheter comes into physical contact with the walls of the urethra and/or bladder. During prolonged periods of catheterisation, this contact can lead to bladder cystitis and spasms.

Most conventional urinary catheters use a balloon located around the exterior of the catheter, and stepped back from the distal tip of the catheter, which is inflated once the catheter is in position in order to retain the catheter in place. When it is time to remove the catheter the balloon must be deflated to permit retraction of the catheter. However, all solid materials have a property known as hysteresis. This is a phenomenon where a material is stretched and does not then return to its original state/length. The effect of hysteresis is proportional to the time and degree of stretching. The balloons used on urinary catheters traditionally were made from latex rubber but since it emerged that there was high incidence of latex allergies, silicone balloons were designed. Compared to latex, silicone experiences a higher degree of hysteresis. When urinary catheter balloons are deflated prior to removal, the membrane that forms the balloon folds into a cuff or ridge around the exterior of the body of the catheter. This is a major cause of concern in silicone catheters which have a higher degree of hysteresis, hence larger cuffs. Although the silicone balloons have a higher degree of cuffing/ridging, it should be noted that latex balloons also form the same cuffs but to a lesser extent. The presence of the cuffed balloon results in an increase in both the effective diameter of the catheter, and the friction generated between the cuffed balloon and, for example, the wall of the urinary tract.

Many research articles have addressed the issues and problems related with cuffing. A number of countries including England and Australia have issued safety notices to warn health workers of probable harm/injury that may be caused due to cuffing. A study in Bristol showed that retention forces due to cuffing of urinary catheter were up to 3N, when removing the catheter, due to the friction generated by the cuffed balloon against the inner wall of the urinary tract. All of the studies identified higher incidence of complications in suprapubic catheters, this being due the fact that supropubic tracts are fibrotic and more resistant to stretching.

Another problem experienced with urinary catheter is that they can be blocked due to obstruction by clots, encrustation, prostate chips or lubricating jelly. In current practice blocked catheters are either irrigated with fluid or changed, which exposes patients to higher chances of infection. In intensive care setting if catheterised patients become anuric (don't produce urine), un-necessary catheter changes are done to out rule possible blocked catheter. Further still in patients with prostate or urethral surgery catheter has to remain in situ for a period of at least two weeks, changing the catheter in this period can jeopardise the surgery. However once a catheter does become blocked it is very difficult to unblock.

Removal of the catheter involves deflating the balloon, the deflated balloon usually forming a wrinkled collar structure, also referred to as a "cuff" or "cuffing" around the, normally smooth, outer surface of the catheter. This enlarged irregular structure impedes retraction of the catheter, and causes discomfort and pain to the patient. Moreover, damage can be caused to the urethral lumen, which increases the risk of acquiring infection.

Indwelling catheters are subject to blockage by, for example, blood clots, debris, and/or crystallisation, requiring irrigation and replacement. This is a time and resource consuming process, which subjects the patient to unnecessary pain, and the stress and anxiety associated therewith. Moreover, the repeated replacement of catheters also greatly increases the risk of infection.

It is therefore an object of the present invention to provide a catheter, which reduces the risk of irritation to the patient, and decreases the discomfort experienced during catheterisation.

SUMMARY OF THE INVENTION

According to the present invention there is provided a catheter comprising a tubular body having a distal end and a proximal end; a retention member displaceable between expanded and contracted states; wherein at least a portion of the retention member, when in the expanded state, projects beyond the distal end of the body.

Preferably, at least a portion of the retention member, when in the expanded state, forms a shroud around and partially beyond the distal end.

Preferably, the retention member, when in the expanded state, prevents contact, in use, between the distal end of the body and a passage into which the catheter is inserted.

Preferably, at least a portion of the retention member, when retracted from the expanded to the collapsed state, is located or can be displaced beyond the distal end.

Preferably, the retention member comprises a resiliently deformable element mounted about an exterior of the body at the distal end.

Preferably, the retention member comprises an inflatable balloon.

Preferably, the retention member, when in the expanded state, is substantially toroidal and extends longitudinally beyond the distal end.

Preferably, the retention member, when in the expanded state, permits fluid flow through the distal end of the body.

Preferably, the retention member, when in the expanded state, is shaped to channel fluid into the distal end of the body Preferably, the catheter comprises a probe operable to remove or reduce blockages about or beyond the distal end of the body.

Preferably, the probe comprises a head located beyond, and displaceable towards and away from, the distal end of the body.

Preferably, the head and the distal end have a complimentary fit in order to occlude the distal end to fluid flow when the head is seated directly against the distal end.

Preferably, the probe comprises an actuator on which the head is mounted, the actuator extending into the body of the catheter and being operable to effect displacement of the head towards and away from the distal end.

Preferably, the actuator comprises a hollow shaft having a bore which is in fluid communication with a conduit which extends through and exits from the head.

Preferably, the probe comprises a plug mounted to the actuator at an end opposite the head, the plug being displaceable into engagement with the proximal end of the body in order to occlude the proximal end to fluid flow.

Preferably, the catheter comprises at least first and second channels about the body, each of the first and second channels being adapted to allow the flow of fluid therethrough.

Preferably, the retention member is in fluid communication with the first channel.

Preferably, the proximal and distal ends of the body are open.

Preferably, the first and/or second channel is formed integrally with a wall of the catheter.

As used herein, the term "user" is intended to mean a person who will undertake the operation of the device during routine use. Usually, this will be a medical professional, where routine use includes insertion of the catheter into the body of a patient. When in use, the invention is oriented so as to have a proximal end and a distal end, each relative to the user.

As used herein, the term "patient" is intended to mean a person on, or in, whom the device will be used during routine operation.

BRIEF DESCRIPTION OF THE DRAWINGS

Embodiments of the invention will now be described by way of example, and in reference to the accompanying drawings, in which.

DETAILED DESCRIPTION OF THE DRAWINGS

Figure 1:
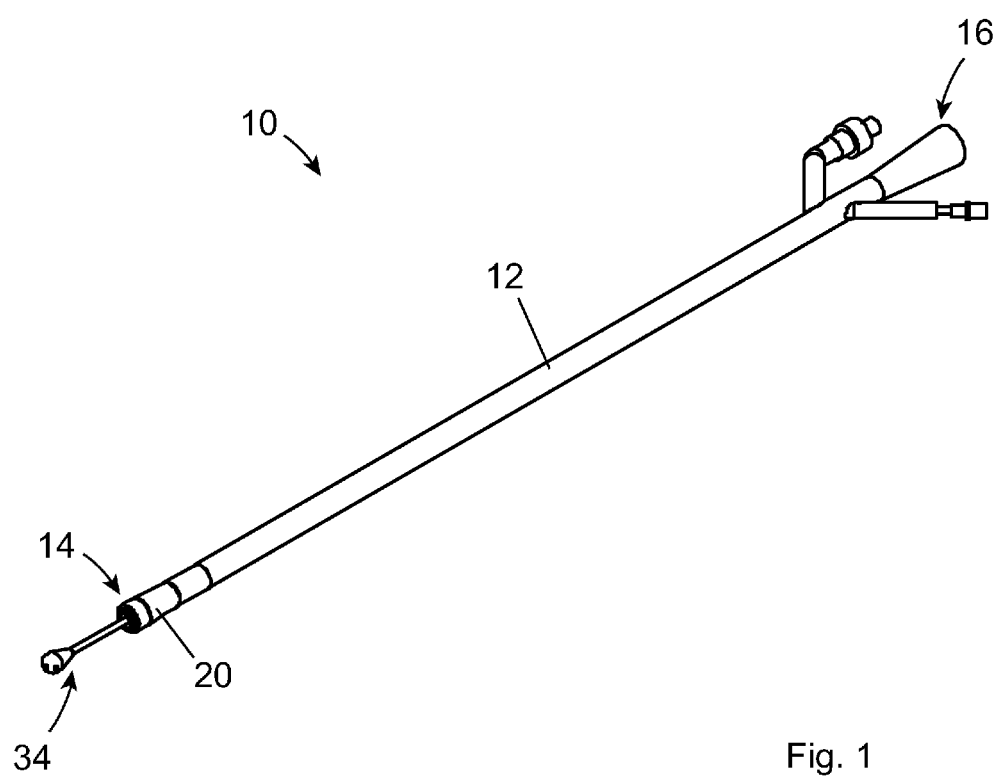
FIG. 1 illustrates a perspective view of a first embodiment of a catheter according to the present invention.
Figure 2:
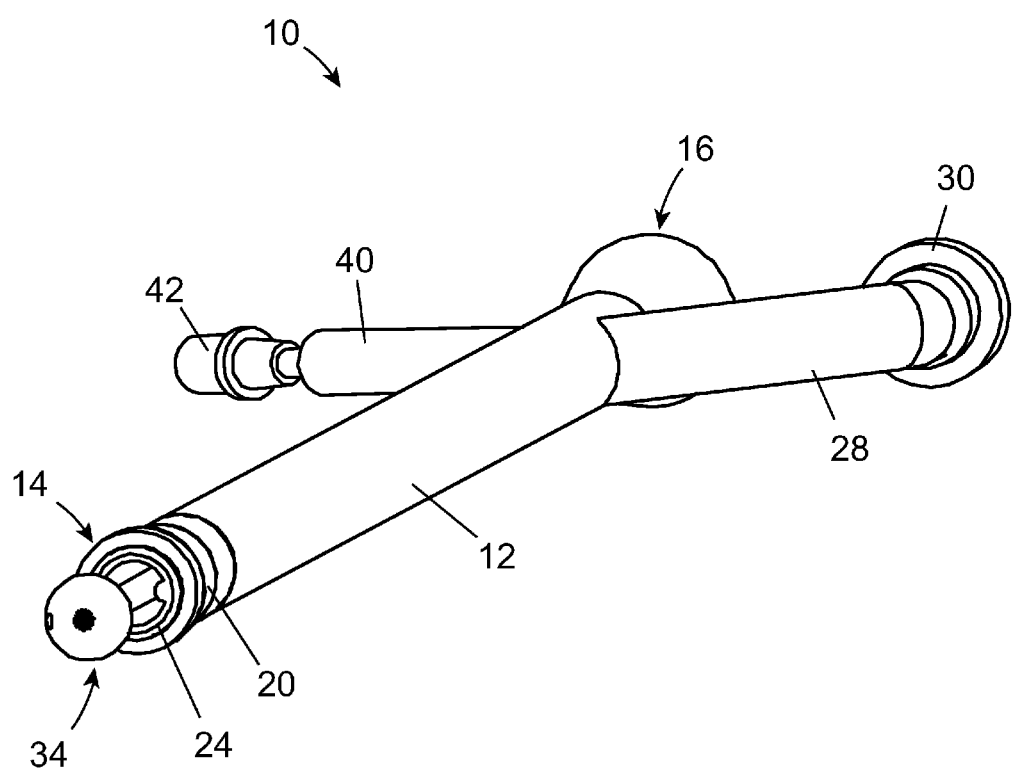
FIG. 2 illustrates an alternative perspective view of the catheter illustrated in FIG. 1.

Referring now to FIGS. 1 to 7 of the accompanying drawings there is illustrated a catheter according to a first embodiment of the present invention, generally indicated as 10, and for use in a number catheterisation practices, for example, urinary catheterisations. The catheter 10 comprises a main body 12 which in the embodiment illustrated is a substantially cylindrical tube having a distal end 14 and a proximal end 16, both of which are open to permit the passage of fluid through the body 12, as will be described in detail hereinafter. The hollow body 12 defines a bore 18 therein, which extends between the distal end 14 and the proximal end 16, and through which fluids such as urine or the like can pass to exit the patient via the catheter 10. The body 12 of the catheter may be formed from any suitable material, and the dimensions may vary to suit the procedure with which the catheter 10 is to be used.

Figure 7:
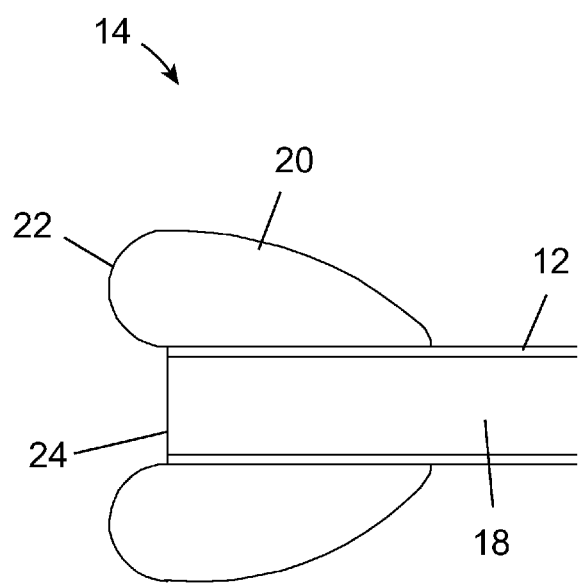
FIG. 7 illustrates an enlarged view of a distal end of the catheter of FIGS. 1 to 6, with a balloon forming part of the catheter in an inflated state.

The catheter 10 further comprises a retention member in the form of an inflatable balloon 20 which is mounted to the exterior of the body 12 and about the distal end 14. The balloon 20 may be fixed to the body 12 in known fashion. The balloon 20 is shown in FIGS. 1, 2, 4 and 5 in a collapsed or retracted state, while FIG. 7 illustrates a schematic representation of the distal end 14, with the balloon 20 in an expanded or inflated state. It can be seen that when in the inflated state the balloon 20 has a flared portion 22 which projects longitudinally beyond a terminal edge 24 of the distal end 14, and thus effectively forms a shroud around the terminal edge 24, which during use of the catheter 10 prevents contact between, for example, the urinary tract/bladder walls and the terminal edge 24 of the catheter 10. This provides a number of benefits, for example, reduction in the possibility of perforation or peritonitis due to erosion of the urinary tract/bladder wall, and the avoidance of tip cystitis, as set out in detail hereinafter.

Figure 3:
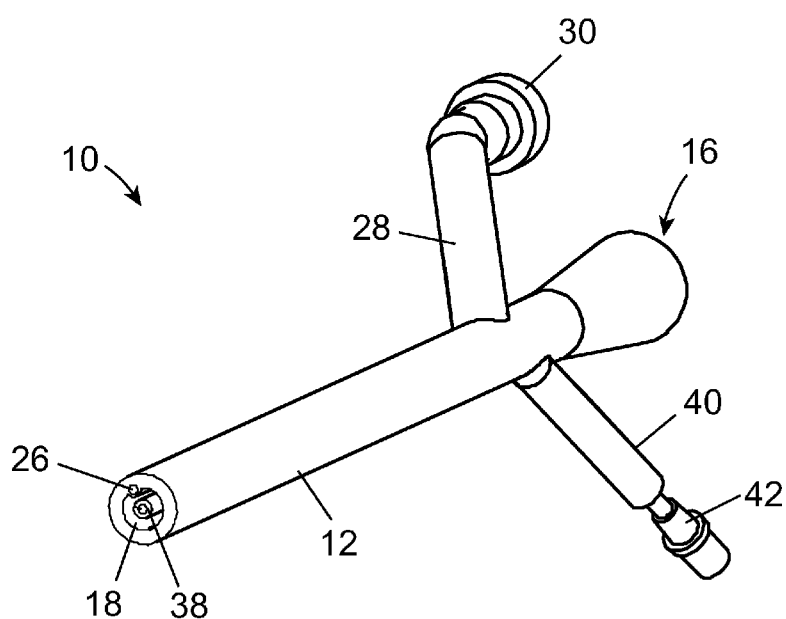
FIG. 3 illustrates a sectioned view of the catheter as illustrated in FIG. 2, revealing the internals of the main body of the catheter.
Figure 5:
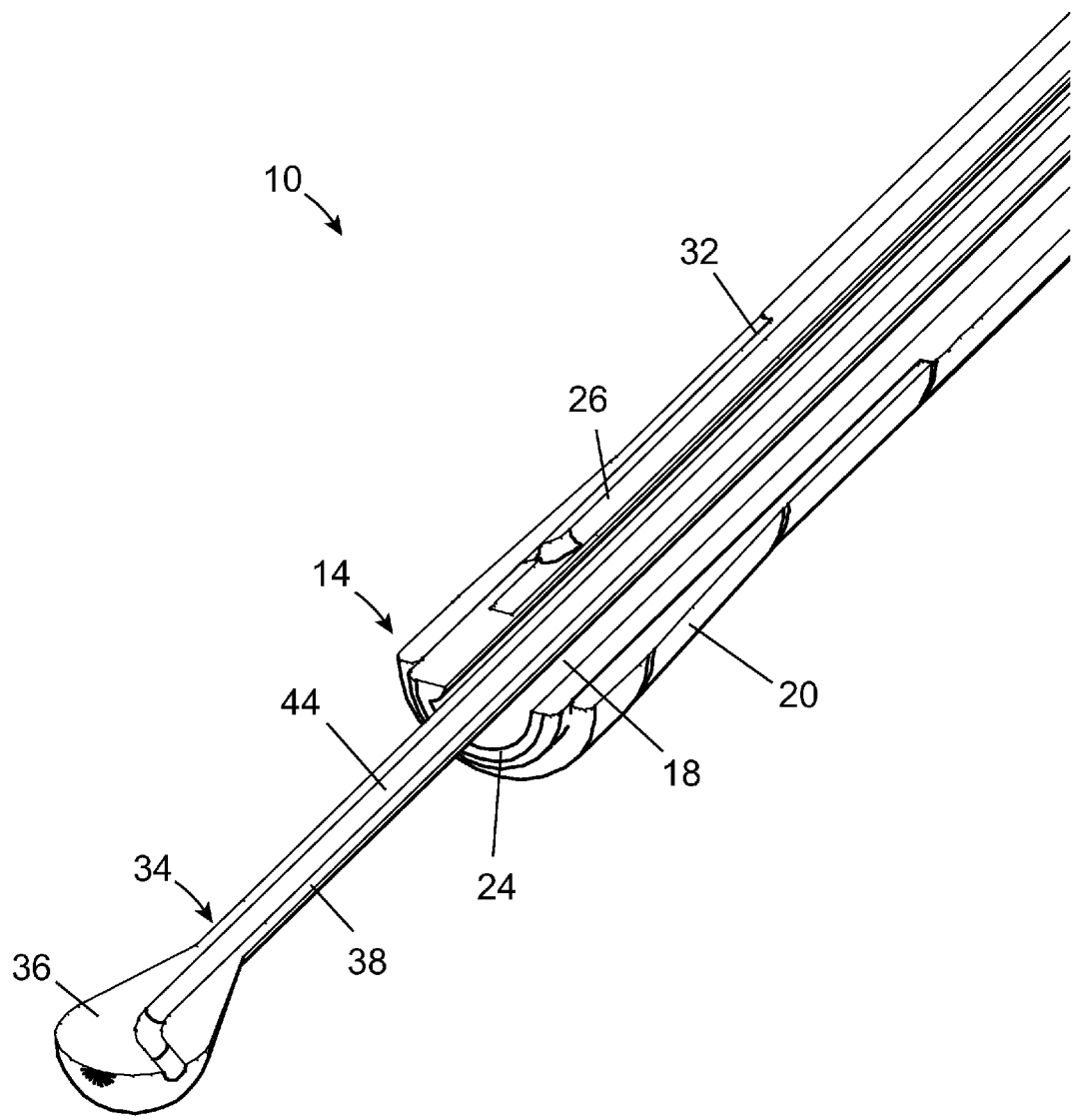
FIG. 5 illustrates a sectioned view of the distal end illustrated in FIG. 4.
Figure 6:
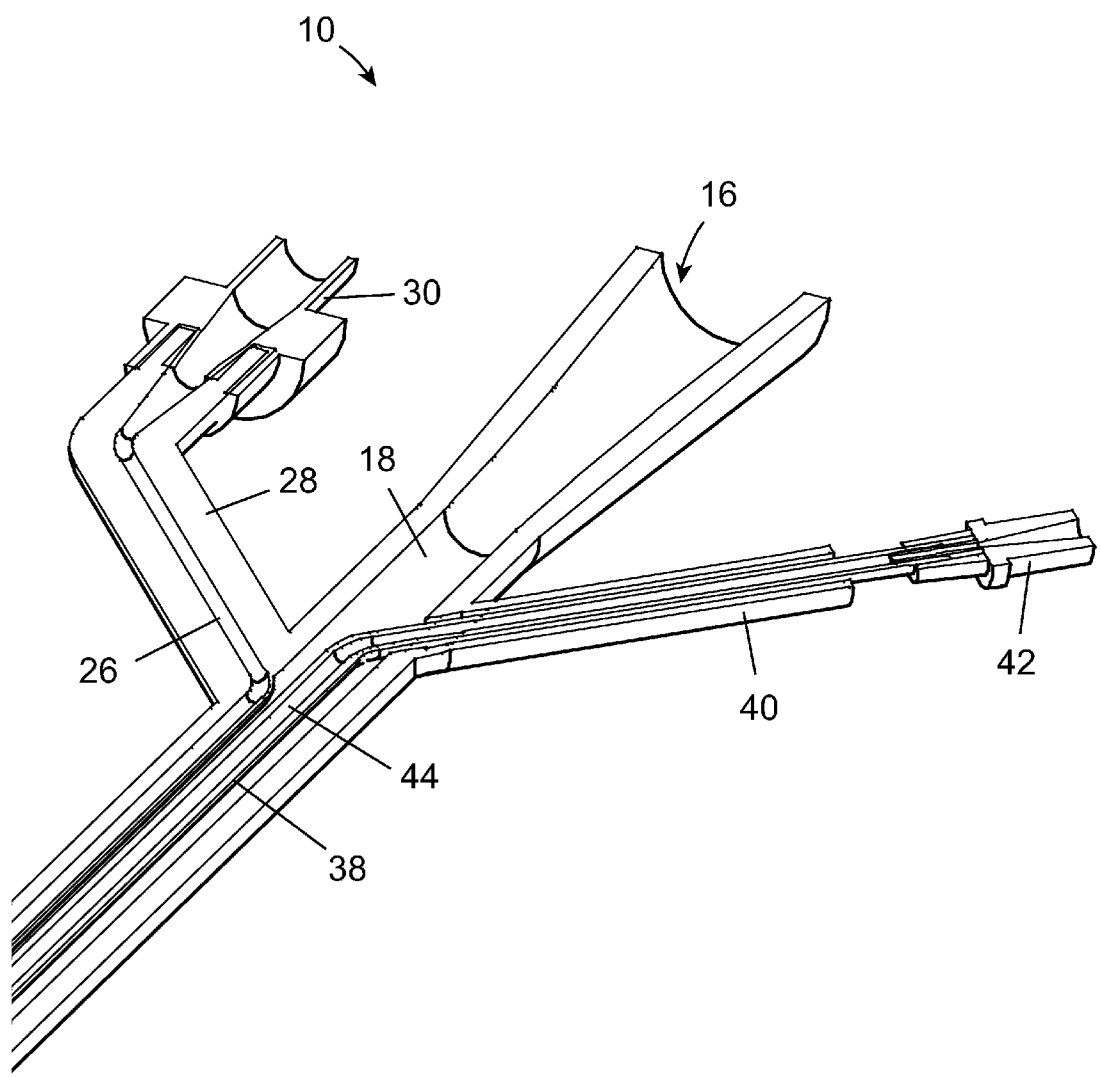
FIG. 6 illustrates a sectioned view of a proximal end of the catheter.

The balloon 20 is displaceable between the collapsed and expanded states, and in the embodiment illustrated this displacement is achieved by filling or emptying the balloon 20 with a fluid or gas, for example, a saline solution. In order to achieve this, the catheter 10 comprises a first channel 26 extending along the length thereof, and in the embodiment illustrated formed integrally with the side wall of the body 12 as shown in FIGS. 3 and 5. It will, however, be appreciated that this first channel 26 could be provided separately of the body 12, for example extending through the bore 18, or possibly located on the exterior of the body 12. The first channel 26 extends rearwardly from the distal end 14 and into a first arm 28 located adjacent the proximal end 16. The first channel 26 terminates at a valve 30 mounted at the end of the first arm 28, which is operable to allow the fluid/gas to be pumped into the balloon 20, following which the valve 30 can be closed during use of the catheter 10 in order to maintain the fluid/gas within the balloon 20 and thus maintain the balloon 20 in the expanded state. Similarly, when it is desired to remove the catheter 10 the first valve 30 can be opened to allow the fluid/gas within the balloon 20 to be drained and thus permit the balloon 20 to be displaced back to the retracted or collapsed state, as will be described in detail below.

The design and position of the balloon 20 result in a significant reduction in the above-mentioned cuffing and thus result in a significant reduction in the force necessary to remove the catheter 10 from a patient. In particular, as the flared portion 22 of the balloon 20 extends beyond the terminal edge 24 of the distal end 14, when the balloon 20 reverts back to the collapsed state, a portion of the collapsed balloon 20 will hang over the end of the terminal edge 24 and thus reduce the amount of the material of the balloon 20 which remains wrapped around the body 12. Thus, the diameter of the catheter 10 at the distal end 14 is substantially the same as the remainder of the body 12. To further reduce the diameter of the catheter 10 about the collapsed balloon 20, the body 12 is preferably provided with a stepped portion 32 (only visible in FIG. 5) of reduced diameter, within which the balloon 20 is located. In this way, and as can be seen, for example, in FIG. 5, the diameter of the catheter 10 about the collapsed balloon 20 can be maintained relatively close to the diameter of the remainder of the body 12, again helping to reduce the force necessary to remove the catheter 10.

By positioning the balloon 20 directly at the distal end 14 of the body 12, and by providing the flared portion 22 which extends longitudinally beyond the terminal edge 24, a number of benefits are achieved. Contact between, for example, the urinary tract/bladder wall and the terminal edge 24 is avoided, thereby reducing or eliminating a number of known issues/complications which arise through the use of conventional catheters, on which the retaining balloon is normally located a significant distance back from the distal end thereof. In addition, the flared portion 22 acts as a shroud, guiding fluids such as urine towards and into the distal end 14, to be withdrawn from the patient by the catheter 10. Finally, when the catheter 10 is to be removed and the balloon 20 is collapsed, by allowing a significant portion of the collapsed balloon 20 to extend beyond the terminal edge 24, cuffing is significantly reduced, thereby reducing the force necessary to remove the catheter 10 and thereby reducing or eliminating the associated problems.

The catheter 10 further comprises a probe 34 which consists of a head 36 located beyond, and displaceable towards and away from, the distal end 14, and an actuator in the form of a tube 38 on which the head 36 is located. The tube 38 extends rearwardly through the bore 18 in the body 12 and through a second arm 40 extending from the body 12 adjacent to the proximal end 16. The tube 38 terminates at the second arm 40 in a coupling 42 which allows the connection of a syringe or the like to the tube 38. The hollow tube 38 defines a second channel 44 which extends into the head 36 and exists from the side of the head 36, as clearly illustrated in FIGS. 4 and 5. In this way, a fluid can be introduced at the coupling 42, and pumped through the second channel 44, to be dispensed from the head 36 of the probe 34. In addition, the tube 38 can be displaced longitudinally within the body 12 by pulling and pushing the coupling 42. In this way, the head 36 can be displaced towards and away from the distal end 14 of the body 12. Thus, the probe 34 and, in particular, the head 36 thereof, can be used in the manner of a plunger to dislodge or break up any blockages which may form in the urinary tract in front of the distal end 14. In addition, in order to minimise the formation of such blockages, the urinary tract/bladder can be irrigated by the pumping of fluid through the second channel 44, which will therefore be ejected or sprayed from the head 36.

Figure 4:
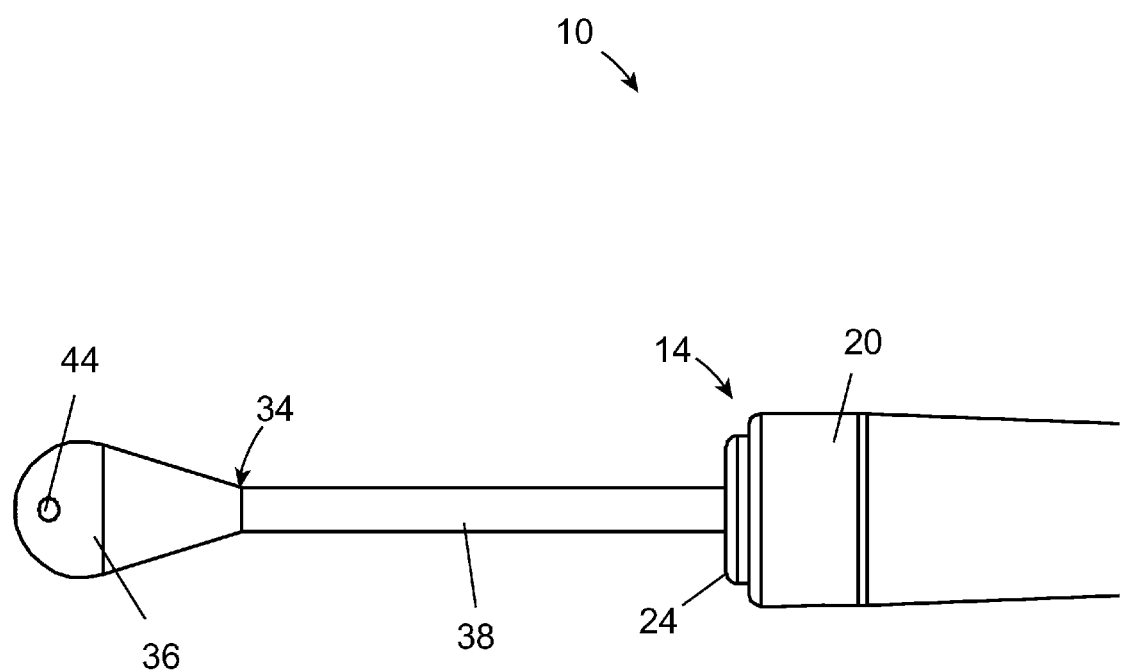
FIG. 4 illustrates an enlarged view of a distal end of the catheter illustrated in FIGS. 1 to 3.

It can also be seen, in particular from FIG. 4, that the head 36 tapers inwardly to join the tube 38. In this way, if the head 36 is drawn towards and into contact with the terminal edge 24 of the distal end 14, the head 36 can form a fluid-tight seal with the terminal edge 24, thus occluding the bore 18 to fluid flow. Thus, the probe 34 can double as an on/off valve for the distal end 14 of the catheter 10. During insertion of the catheter 10 the head 36 is preferably drawn into contact with the terminal edge 24 in order to provide a smooth round and thus atraumatic tip to the catheter 10. Once the catheter 10 has been inserted the coupling 42 is displaced into contact with the end of the second arm 40 in order to displace the head 36 away from the terminal edge 24 so that the drainage of urine can begin. The outer surface of the tube 38 should have a close fit with the internal surface of the second arm 40 in order to prevent the leakage of urine from the second arm 40, in particular during manipulation of the head 36 via the coupling 42. The coupling 42 is also preferably provided with a stopper or plug (not shown) locatable in the open end thereof in order to seal the second channel 44 when not being used for irrigation purposes.

It will be appreciated that the tube 38, rather than having an elbowed transition between the main body 12 and the second arm 40, could extend straight out of the proximal end 16 of the main body 12, with the second arm 40 then being used as the drainage channel for urine. It should also be noted that if the catheter 10 is being used for suprapubic drainage the probe 34 and second arm 40 may be omitted.

Figure 8:
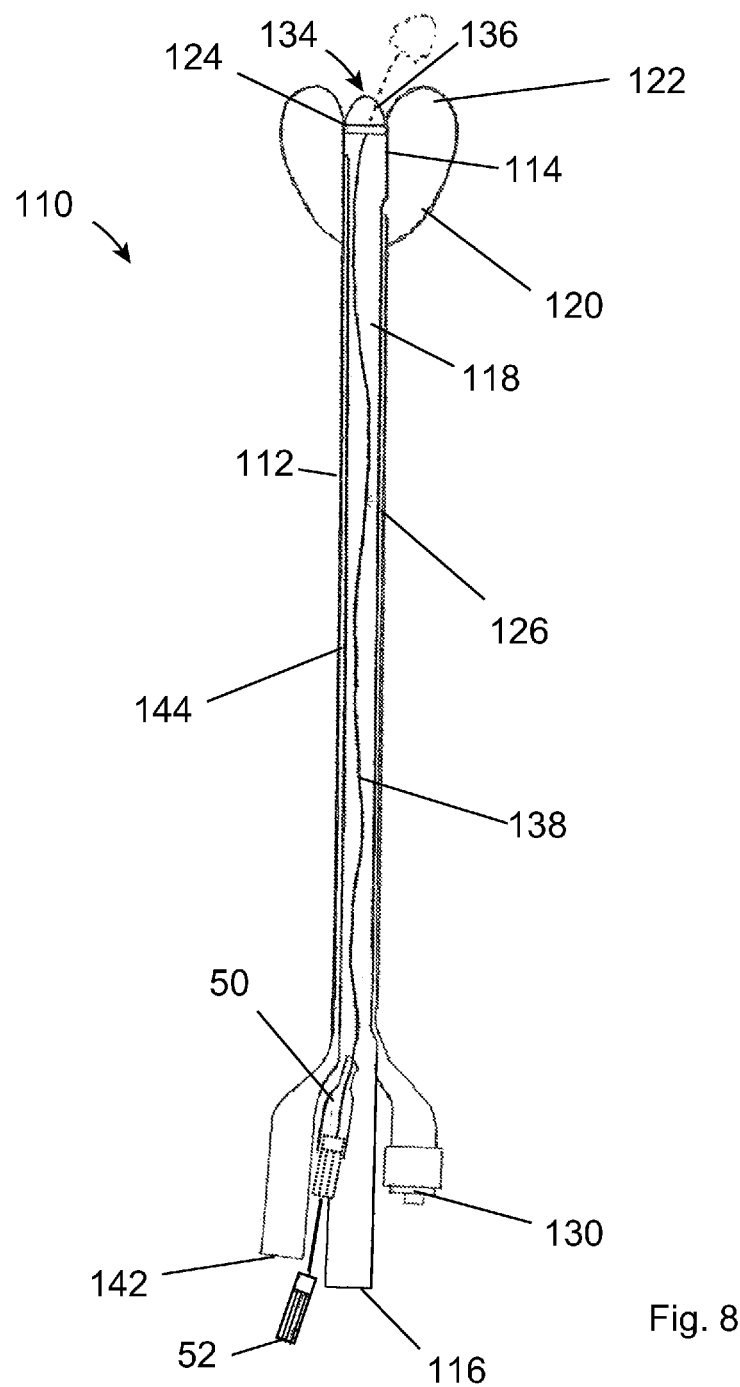
FIG. 8 illustrates a schematic view of a catheter according to a second embodiment of the present invention.

Referring now to FIG. 8, there is shown a second embodiment of a catheter according to the present invention, generally indicated as 110. In this second embodiment like components have been accorded like reference numerals, and unless otherwise stated, perform a like function. The catheter 110 has a generally cylindrical shaped body 112, having a distal end 114 and a proximal end 116, between which extends a bore or lumen 118 for the passage of fluid through the catheter 110. A retention member in the form of an inflatable balloon 120, depicted in the inflated or expanded state, is located adjacent a terminal edge 124 of the distal end 114 of the catheter 110.

In the collapsed or retracted state, the balloon 120 is retained about the outer surface of the body 112, and may be contained within a stepped or recessed portion (not shown) of the body 112. In the inflated state, the balloon 120 is generally toroidal in form, and is substantially heart shaped in cross section, with a flared portion 122 of the balloon 120 extending longitudinally beyond the terminal edge 124 of the distal end 114. A first channel 126, having open opposing ends, is provided within the lumen of the catheter 10. The first channel 124 is generally cylindrical in shape, the distal end of which is in fluid communication with the balloon 120. A fluid (not shown) can be introduced at the proximal end 116 using, for example, a syringe (not shown), to inflate the balloon 120. A valve 130 is provided at the proximal end of the first channel 124, which allows the fluid to be retained in the balloon 120 and the first channel 124.

A second channel 144, having open opposing ends, is provided within the central bore or lumen 118 of the catheter 110. The second channel 144 is generally cylindrical in shape, the distal end of which opens adjacent the terminal edge 124 of the distal end 114 of the catheter 110. The proximal end of the second channel 144 has a coupling in the form of an open mouth 142, which is adapted to receive a syringe (not shown), or similar device, to allow a fluid (not shown) to be introduced into the second channel 144, facilitating irrigation of the distal end 114 of the catheter 110. The lumen 118 of the catheter 110 is adapted to allow the passage of a fluid (not shown) therethrough, for example urine. The proximal end 116 of the catheter is open and adapted to be in fluid communication with a receptacle, such as a drainage bag, or similar device (not shown).

The catheter 110 further comprises a probe 134 having a head 136 located about the distal end 114, and an actuator in the form of a wire 138 extending from the head 136 along at least part of the length of the lumen 118 of the catheter 110. The head 136 is generally tapered in form, and is shaped and dimensioned to be reversibly retained at the terminal edge 124 of the distal end 114. An outlet 50 is located at the proximal end 116 of the catheter 110. The end of the wire 138 passes from the lumen 118 of the catheter 110, and through the outlet 50. A stopper 52 is located at the proximal end of the wire 138. The stopper 52 is shaped and dimensioned to be reversibly engageable with the outlet 50, and capable of forming a fluid-tight engagement therewith.

When used, for example, for male urinary catherisation, the catheter 110 is provided having the balloon 120 in a collapsed state, and with the head 136 engaging the terminal edge 124 of the distal end 114. Following insertion into the urethra, a fluid such as sterile saline can be introduced into the first channel 126, in order to inflate the balloon 120. The shape and dimension of the inflated balloon 120 provides a barrier or shroud between the urethra and the catheter 10, in particular the terminal edge 124, thereby reducing the risk of irritation of the urethra. The valve 130 will retain said fluid, thereby retaining the balloon 120 in the inflated state. A drainage bag or similar receptacle (not shown) can be secured in fluid communication with the open proximal end 116 of the catheter 110.

The stopper 52 can then be engaged with the outlet 50 (depicted in broken lines), thereby providing a fluid-tight seal. The wire 138 is advanced along the lumen 118 of the catheter 110, and as a result the head 136 (depicted in broken lines), is disengaged from the terminal edge 124 of the distal end 114 thereby allowing the passage of fluid such as urine through the lumen 118 of the catheter 110 to the drainage bag or similar receptacle. The urethra can be irrigated by a fluid such as sterile saline by introducing said fluid at the coupling 142 of the second channel 144 using a syringe or similar device (not shown). Blockages occurring due to, for example, blood clots in the urine can be removed by manipulation of the wire 138 in order to displace the head 136 in the form of a plunger to dislodge and/or break up such blockages.

To remove the catheter 110, the fluid is removed from the first channel 126, in order to collapse the balloon 120. During withdrawal of the catheter 110, the collapsed balloon 120 will occupy the space succeeding the distal end 114 of the catheter 110. As a result the collapsed balloon 120 does not increase the outer diameter of the catheter 110, reducing discomfort of the patient during removal thereof.

Thus in summary the catheter 10; 110 of the present invention provides a number of advantages over conventional catheters, namely:

1. Non Cuffing helps during removal of the catheter because
   a. Facilitates easier and quicker removal of catheter
   b. Less pain/bladder spasms
   c. Minimal urethral damage
   d. Prevents anastomotic damage in patients with urethral surgery/injury
   e. Prevents bladder-urethral anstomosis breakdown after prostate surgery
   f. Minimises spontaneous tract closure when changing supra pubic catheter
   g. Less bleeding from suprapubic site
2. The absence of a closed tip on the catheter helps because
   a. Less foreign material in bladder
   b. Less chance of perforation/peritonitis due to erosion of bladder wall
   c. No tip cystitis
   d. Less bladder spasms
   e. Less chance of bladder muscle over activity
   f. Since minimises cystitis chance of bladder cancer decrease
3. No Blocking helps
   a. In haematuria with clots
   b. Allows from breaking bladder clots
   c. More thorough irrigation
   d. Minimises infection since clots can be broken down and drained
   e. Prevents unnecessary catheter changes
   f. User friendly unblocking mechanism
   g. Helps differentiate between anuric patient or blocked catheter
   h. Dislodges any debris within lumen

The invention claimed is:

1. A catheter comprising:
   a tubular body having a distal end and a proximal end and a first exterior facing surface; and
   a retention member displaceable between expanded and contracted states;
   wherein at least a portion of the retention member, when in the expanded state, projects beyond the distal end of the body;
   the catheter further comprising a probe which comprises a head having a tip with an end, where the end is smooth and rounded, where the head is located beyond and displaceable towards and away from the distal end of the body, and an actuator on which the head is mounted, the actuator extending into the body of the catheter and being operable to effect displacement of the head towards and away from the distal end of the body,
   in which the head is tapered inwardly so that it is shaped to be drawn into the distal end of the body to form a fluid-tight seal;
   wherein the actuator comprises a hollow shaft having a bore which is in fluid communication with a conduit which extends through and exits from the head at a port located on a second exterior facing surface of the head such that after the head is drawn into the distal end of the body to form the fluid-tight seal, the port remains exposed to an exterior outside of the first exterior facing surface and the second exterior facing surface.

2. A catheter according to claim 1 in which at least a portion of the retention member, when in the expanded state, forms a shroud around and partially beyond the distal end.

3. A catheter according to claim 2 in which the retention member, when in the expanded state, prevents contact, in use, between the distal end of the body and a passage into which the catheter is inserted.

4. A catheter according to claim 1 in which at least a portion of the retention member, when retracted from the expanded to the collapsed state, is located or can be displaced beyond the distal end.

5. A catheter according to claim 1 in which the retention member comprises a resiliently deformable element mounted about an exterior of the body at the distal end.

6. A catheter according to claim 1 in which the retention member comprises an inflatable balloon.

7. A catheter according to claim 1 in which the retention member, when in the expanded state, is substantially toroidal and extends longitudinally beyond the distal end.

8. A catheter according to claim 1 in which the retention member, when in the expanded state, permits fluid flow through the distal end of the body.

9. A catheter according to claim 1 in which the retention member, when in the expanded state, is shaped to channel fluid into the distal end of the body.

10. A catheter according to claim 1 in which the probe comprises a plug mounted to the actuator at an end opposite the head, the plug being displaceable into engagement with the proximal end of the body in order to occlude the proximal end to fluid flow.

11. A catheter according to claim 1 comprising at least first and second channels about the body, each of the first and second channels being adapted to allow the flow of fluid therethrough.

12. A catheter according to claim 11 in which the retention member is in fluid communication with the first channel.

13. A catheter according to claim 1 in which the proximal and distal ends of the body are open.

14. A catheter according to claim 11 in which the first and/or second channel is formed integrally with a wall of the catheter.

* * * * *